US006370223B1

(12) United States Patent
Gleason et al.

(10) Patent No.: US 6,370,223 B1
(45) Date of Patent: Apr. 9, 2002

(54) AUTOMATIC DETECTION OF BONE FRAGMENTS IN POULTRY USING MULTI-ENERGY X-RAYS

(75) Inventors: Shaun S. Gleason; Michael J. Paulus; James A. Mullens, all of Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/827,876

(22) Filed: Apr. 6, 2001

(51) Int. Cl.⁷ .............................................. G01B 15/06
(52) U.S. Cl. .......................................... 378/58; 378/54
(58) Field of Search .............................. 378/51, 53, 54, 378/58, 98.9

(56) References Cited

U.S. PATENT DOCUMENTS

| | | | | |
|---|---|---|---|---|
| 3,854,049 A | * | 12/1974 | Mistretta et al. ............ | 250/402 |
| 5,428,657 A | * | 6/1995 | Papanicolopoulos et al. | 378/86 |
| 5,841,833 A | | 11/1998 | Mazess et al. | |
| 5,902,177 A | | 5/1999 | Tessier et al. | |
| 6,038,028 A | * | 3/2000 | Grann et al. ................. | 356/381 |
| RE36,664 E | | 4/2000 | O'Brien et al. | |

OTHER PUBLICATIONS

J. C. Wyvill, "The Development of an On–Line X–ray System that Accurately Detects Bone and Cartilage Fragments in Poultry Meat", U.S. Poultry & Egg Association, 1530 Cooledge Road, Tucker, Georgia 30084–7303, www.poultryegg.org/research/proj 080.htm, Mar. 1994.

J. S. Marks, et al., "Nuclear Magnetic Resonance for Poultry Meat Fat Analysis and Bone Chip Detection", U.S. Poultry & Egg Association, 1530 Cooledge Road, Tucker, Georgia 30084–7303, http://www.poultryegg.org/research/proj 083.htm, Feb. 1998.

R. E. Alvarez and A. Macovski, "Energy–Selective Reconstructions in X–ray Computerized Tomography", Phys. Med. Biol. 21, 733–744 (1976).

S. S. Gleason, J. A. Mullens, M. J. Paulus, "Next–Generation Reconstruction Algorithms for Computed Tomprography: Seed Money Final Report", ORNL Seed Money Final Report, Account # 3210–001 Y (Dec., 1999).

* cited by examiner

Primary Examiner—Robert H. Kim
Assistant Examiner—Jurie Yun
(74) Attorney, Agent, or Firm—James M. Spicer

(57) ABSTRACT

At least two linear arrays of x-ray detectors are placed below a conveyor belt in a poultry processing plant. Multiple-energy x-ray sources illuminate the poultry and are detected by the detectors. Laser profilometry is used to measure the poultry thickness as the x-ray data is acquired. The detector readout is processed in real time to detect the presence of small highly attenuating fragments in the poultry, i.e., bone, metal, and cartilage.

8 Claims, 2 Drawing Sheets

AUTOMATIC DETECTION OF BONE FRAGMENTS IN POULTRY USING MULTI-ENERGY X-RAYS

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

This invention relates to the inspection of meat products by x-ray means. More particularly, it relates to the fast determination of small bone fragments and other dense objects in conveyed meat products.

2. Background Information

Screening for bone and cartilage fragments in deboned poultry has become a major concern for the poultry industry. Manual palpation techniques are less than accurate, and pose a risk of spreading microbial contamination. Bones left in meat, in turn, result in product liability actions and shipment returns for rework with staggering cost implications [1], [2].

In recent years, x-ray systems have begun to emerge in bone screening applications. These systems look for differences in density from the raw poultry meat and bone or other foreign matter. Unfortunately, at the x-ray energies these systems typically employ, the density differences between bone and cartilage fragments and the raw meat itself are very small. In addition, the natural density variance in raw meat (created by water and fat) and meat thickness differences make it extremely difficult for simple transmission X-ray methods to accurately discriminate bone and cartilage.

The fraction of an x-ray beam that will penetrate an object is governed by the expression $$I = I_0 \exp\left(-\int_l \mu(E, x) dx\right)$$

where $I_0$ is the intensity of the incident x-ray beam, I is the intensity of the x-ray beam penetrating the object, $\mu(E,x)$ is the position and energy dependent x-ray attenuation coefficient, and 1 is the x-ray path length. The ratio $I/I_0$ therefore depends upon the material properties of the object, the energy of the x-ray beam and the thickness of the object. Traditional x-ray screening systems measure only I, and therefore cannot consider the energy dependence of the attenuation coefficient or compensate for variations in the path length. Variations in the sample thickness can also prevent detection of foreign matter. If these thickness variations are known, however, mathematical compensation may be introduced.

Unlike traditional x-ray screening systems, which only measure I in Equation 1, the proposed system measures both I and $I_0$ at several energies, and independently determines the x-ray path length. By more thoroughly measuring the parameters of Equation 1, the methods described below may be used to achieve greater sensitivity to bone, cartilage and other foreign fragments, and hence faster determinations of their presence in the poultry products.

A recent patent features dual x-ray scanners and simultaneous scanning of the interior and exterior portions of an animal carcass (U.S. Pat. No. Re. 36,664; Issued Apr. 18, 2000). Designed for segmenting animal carcasses, it is not adapted for making quick determinations of small bone fragments.

Another recent patent, also from the meat cutting field, employs flashing light sources or a single x-ray source to obtain rib thickness data of large animals (U.S. Pat. No. 5,902,177; Issued May 11, 1999). This patent also utilizes a laser ranging method for obtaining surface profile data.

While the above methods are suitable for segmenting large animal carcasses, they are not adapted for the quick determination of small bone fragments and other similarly dense objects in, for example, chicken breasts of non-uniform thickness traveling on a moving conveyor system.

In the medical imaging field, there have been several examples of the use of x-rays at two different energies to precisely distinguish bone and cartilage from muscle and fat. One patent features a switched-mode dual energy x-ray system where the different x-ray energies are obtained by periodic switching of the x-ray source voltage (U.S. Pat. No. 5,841,833, Issued Nov. 24, 1998).

Other References

1) "The Development of an On-Line X-Ray System that Accurately Detects Bone and Cartilage Fragments in Poultry Meat", U.S. Poultry & Egg Association, 1530 Cooledge Road, Tucker, Ga. 30084-7303.

2) "Nuclear Magnetic Resonance for Poultry Meat Fat Analysis and Bone Chip Detection", U.S. Poultry & Egg Association, 1530 Cooledge Road, Tucker, Ga. 30084-7303.

3) R. E. Alvarez and A. Macovski, "Energy-Selective Reconstructions in X-ray Computerized Tomography", Phys. Med. Biol. 21, 733–744 (1976).

4) S. S. Gleason, J. A. Mullens, M. J. Paulus, "Next-Generation Reconstruction Algorithms for Computed Tomography: Seed Money Final Report", ORNL Seed Money Final Report, Account # 3210-001Y (December, 1999).

BRIEF SUMMARY OF THE INVENTION

At least two linear x-ray detectors are positioned below a conveyor belt in a poultry processing plant. At least two x-ray sources, each producing a different energy x-ray, are positioned above the conveyor belt for radiating the poultry. The x-rays that pass through the poultry, i.e., those that are not absorbed, are measured by the detectors. Laser profilometry is used to measure the chicken thickness as the x-ray data is acquired. The thickness data is used to compensate the x-ray profile measurement so that the x-ray attenuation will be accurately determined. The detector readout is processed in real time to detect the presence of highly attenuating fragments in the poultry such as bone, metal, or cartilage. A multiple-energy x-ray system has greater sensitivity to such foreign particles than a single energy system. It is believed that sub-millimeter resolution can be achieved.

DETAILED DESCRIPTION OF THE INVENTION

First Embodiment

Figure 1:
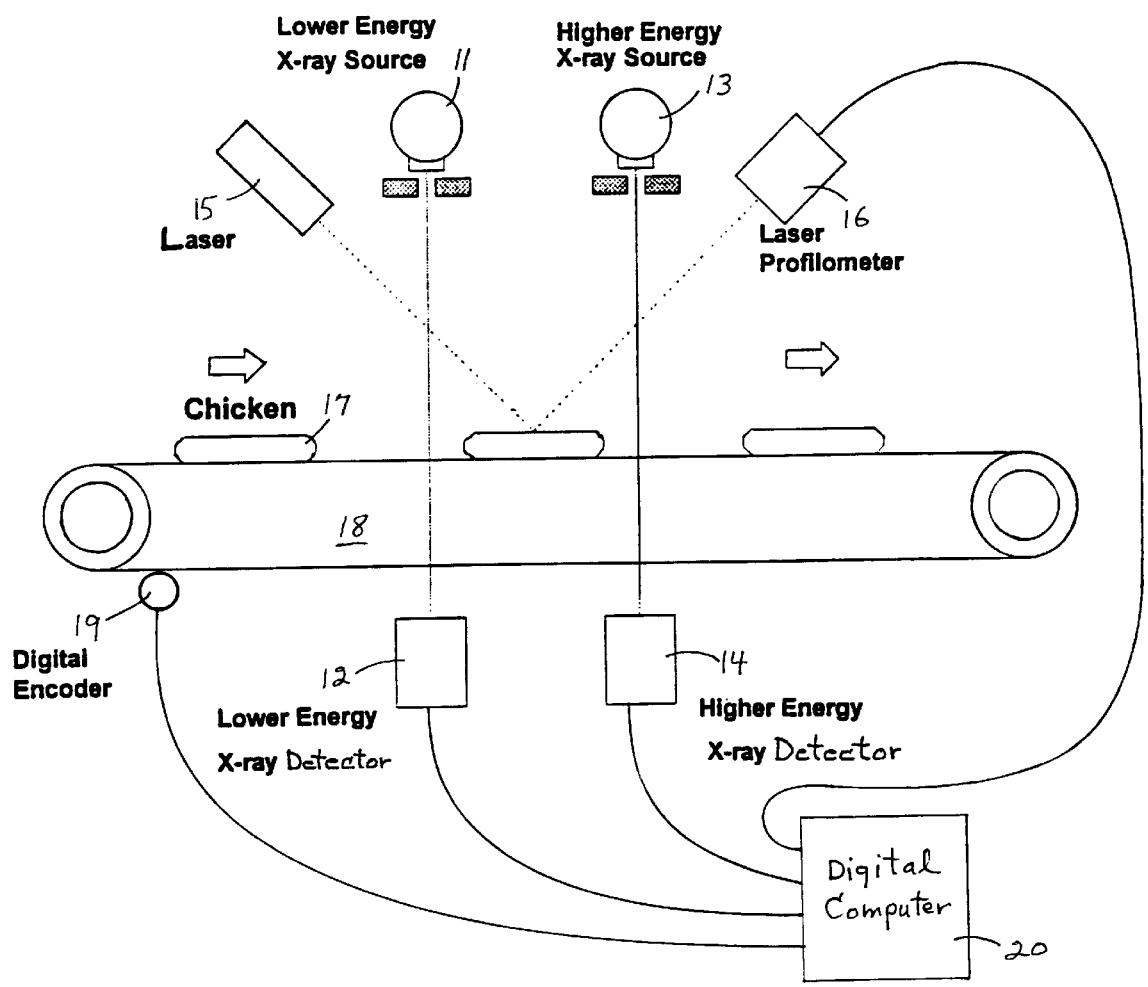
FIG. 1 illustrates a system according to the invention for determining the presence of bone fragments in conveyed meat products using signals from multiple energy x-ray systems and a surface profile signal.

A first embodiment of the invention is shown in FIG. 1. In FIG. 1, a lower energy x-ray source 11 generates x-rays that are passed through a plane of a meat product 17 riding on a conveyor belt 18. The x-rays that pass through the meat product are detected by a linear x-ray detector 12. This detector may be a linear diode array coupled to a phosphor screen, a linear CCD array coupled to a phosphor screen, a multi-anode photomultiplier tube coupled to a phosphor screen, or high-Z semiconductor detector arrays of germanium, cadmium zinc telluride, etc. The measured x-ray flux is stored in a digital computer 20 as an x-ray attenuation profile through the plane of the meat product. The meat product 17 moves beneath at least a second higher-energy x-ray source 13 whose x-rays are passed through the meat product and detected by a second linear x-ray detector 14. The measured x-ray flux from the second x-ray detector is used to generate a second x-ray attenuation profile. The movement of the meat product on the conveyor belt is monitored by means of a digital encoder so that the attenuation profiles measured by the at least two x-ray detectors may be synchronized to the same cross-sectional plane through the meat product.

In addition to the two linear x-ray attenuation profile measurements, a surface height profile is also measured using a combination of a laser 15 and a laser profilometer 16. The laser profilometer 16 is comprised of a solid-state camera (CMOS or CCD) and a microprocessor (not shown). The microprocessor is used to extract from the image the surface height profile projected across the top of the meat product. The digital computer 20 synchronizes this height profile measurement of the meat product to the at least two x-ray profile measurements using the information obtained from the digital encoder 19.

Separate profile measurements of the Compton scattering and photoelectric absorption interaction mechanisms are generated by exploiting the different energy dependencies of the at least two primary x-ray interaction mechanisms using the method of Alvarez [3]. The energy-dependence of the attenuation coefficient may be written:

$$\mu(x,y,E) = \mu_{PE}(x,y) f_{PE}(E) + \mu_{CS}(x,y) f_{CS}(E)$$

where $f_{PE}(E)$ and $f_{CS}(E)$ are known functions of energy associated with the photoelectric and Compton scattering interactions. Using the multi-energy x-ray systems of the invention, separate x-ray attenuation profiles associated with the two attenuation coefficients, $\mu_{PE}(x,y)$ and $\mu_{CS}(x,y)$, are constructed. The importance of constructing such profiles stems from the fact that the photoelectric interaction, conveyed by $\mu_{PE}(x,y)$, is a strongly increasing function of atomic number and thus reflects the molecular composition of the meat type (or meat state). Compton scattering, conveyed by $\mu_{CS}(x,y)$, depends on the electron density, which is related to the mass density of the meat. Separate profiles of these interaction mechanisms provide information of new diagnostic value as demonstrated in our earlier work [4].

Figure 2:
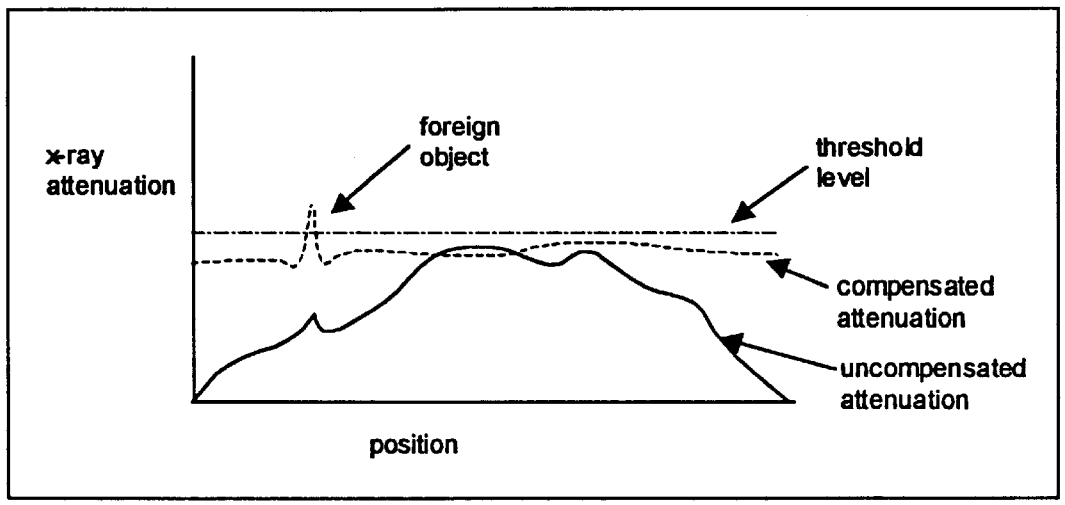
FIG. 2 is a graph of x-ray attenuation vs. lateral position along a meat product that is illustrative of the result produced by a first preferred embodiment of the invention. Both uncompensated and compensated attenuation profiles are shown, as well as a threshold level applied to either a thickness compensated photoelectric absorption profile or a thickness compensated Compton scattering x-ray attenuation profile.

Once these at least two new x-ray attenuation profiles are determined, the surface height profile (as measured by the laser and laser profilometer) is used to compensate these profiles. This compensation involves normalizing the x-ray attenuation profiles by the thickness of the meat to calculate the average attenuation coefficient of the meat along the x-ray line integrals from the x-ray sources to the x-ray detector elements. An example of this compensation on one of these two profiles (either the thickness compensated Compton scattered profile or the thickness compensated photoelectric absorption profile) is shown in FIG. 2.

Once the compensation of the profiles has been performed, a threshold level is set that is consistent with the expected average attenuation of the meat being inspected. Any part of the compensated profile that exceeds the preset threshold will be flagged as the position of a foreign object (bone, cartilage, metal, etc.). This preset threshold for either the thickness compensated Compton scattered profile or the thickness compensated photoelectric absorption profile is also shown in FIG. 2.

Second Embodiment

The second embodiment of the invention is like the first embodiment in many respects. Referring again to FIG. 1, this time to explain the second embodiment, a lower energy x-ray source 11 generates x-rays that are passed through a plane of a meat product 17 riding on a conveyor belt 18. The x-rays that pass through the meat product are detected by a linear x-ray detector 12. This detector may be a linear diode array coupled to a phosphor screen, a linear CCD array coupled to a phosphor screen, a multi-anode photomultiplier tube coupled to a phosphor screen, or high-Z semiconductor detector arrays of germanium, cadmium zinc telluride, etc. The measured x-ray flux is stored in the digital computer 20 as an x-ray attenuation profile through the plane of the meat product. The meat product 17 moves beneath at least a second higher-energy x-ray source 13 whose x-rays are passed through the meat product and detected by a second linear x-ray detector 14. The measured x-ray flux from the second x-ray detector is used to generate a second x-ray attenuation profile. The movement of the meat product on the conveyor belt is monitored by means of a digital encoder so that the attenuation profiles measured by the at least two x-ray detectors may be synchronized to the same cross-sectional plane through the meat product.

In addition to the two linear x-ray attenuation profile measurements, a surface height profile is also measured using a combination of a laser 15 and a laser profilometer 16. The laser profilometer 16 is comprised of a solid-state camera (CMOS or CCD) and a microprocessor (not shown) that is used to extract from the image the surface height profile projected across the top of the meat product. The digital computer 20 synchronizes this height profile measurement of the meat product to the at least two x-ray profile measurements using the information obtained from the digital encoder 19.

The multi-energy x-ray attenuation profiles are combined linearly (e.g. scaled and subtracted) to form a new x-ray attenuation profile. This is similar to what is done in dual energy x-ray absorption systems but, in this second embodiment of the invention, the operation is extended to allow linear combinations of multiple (more than two) x-ray attenuation profiles, each captured using a different x-ray energy.

Figure 3:
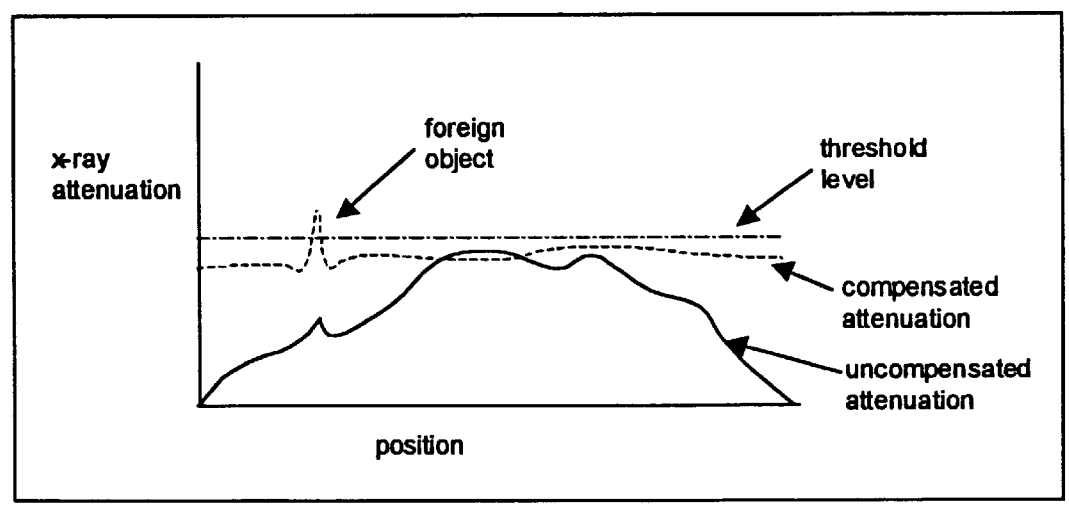
FIG. 3 is a graph of x-ray attenuation vs. lateral position along a meat product that is illustrative of the result produced by a second preferred embodiment of the invention. Both uncompensated and compensated attenuation profiles are shown, as well as a threshold level applied to a thickness compensated enhanced line scan x-ray attenuation profile.

Once this new, linearly combined x-ray attenuation profile is determined, the surface height profile (as measured by the laser and laser profilometer) is used to compensate this profile. This compensation involves normalizing the x-ray attenuation profiles by the thickness of the meat product to calculate the average attenuation coefficient of the meat product along the x-ray line integrals from the x-ray sources to the x-ray detector elements. This compensation is shown in FIG. 3.

Once the compensation of the new profile has been performed, a threshold level is set that is consistent with the expected average attenuation of the meat product being inspected. Any part of the compensated profile that exceeds the preset threshold will be flagged as the position of a foreign object (bone, cartilage, metal, etc.). This preset threshold is also shown in FIG. 3.

What is claimed is:

1. A method for detecting a higher density object in a lower density meat product comprising the steps of:
   a) obtaining a first line scan x-ray attenuation profile along a plane through the meat product using a first energy x-ray;
   b) obtaining at least a second line scan x-ray attenuation profile in the same plane through the meat product using a different energy x-ray;
   c) obtaining a surface profile of the meat product in the same plane through the meat product;
   d) modeling the photoelectric absorption using the line scan x-ray attenuation profiles to obtain a modified photoelectric absorption attenuation profile;
   e) modeling the Compton scattering effect using the line scan x-ray attenuation profiles to obtain a modified Compton scattering x-ray attenuation profile;
   f) performing a thickness compensation of the modified photoelectric absorption attenuation profile and modified Compton scattering x-ray attenuation profile using the surface profile; and
   g) applying threshold levels to the thickness compensated modified photoelectric absorption attenuation profile and thickness compensated modified Compton scattering x-ray attenuation profiles.

2. A method for detecting a higher density object in a lower density meat product comprising the steps of:
   a) obtaining a first line scan x-ray attenuation profile along a plane through the meat product using a first energy x-ray;
   b) obtaining at least a second line scan x-ray attenuation profile in the same plane through the meat product using a different energy x-ray;
   c) obtaining a surface profile of the meat product in the same plane through the meat product;
   d) linearly combining the line scan x-ray attenuation profiles to obtain an enhanced line scan x-ray attenuation profile;
   e) performing a thickness compensation of the enhanced line scan x-ray attenuation profile; and
   f) applying a threshold level to the thickness compensated enhanced line scan x-ray attenuation profile.

3. A density determining apparatus for detecting a higher density object in a lower density meat product comprising:
   a) a first x-ray source producing x-rays of a first energy;
   b) a first linear x-ray detector for obtaining a first line scan x-ray attenuation profile along a plane through the meat product using the first energy x-rays;
   c) at least a second x-ray source producing x-rays of a second energy;
   d) at least a second linear x-ray detector for obtaining a second line scan x-ray attenuation profile in the same plane through the meat product using the second energy x-rays;
   e) a surface profiling means for obtaining a surface profile of the meat product in the same plane through the meat product;
   f) a processor for modeling the photoelectric absorption and Compton scattering effects using the line scan x-ray attenuation profiles to obtain a modified photoelectric absorption attenuation profile and a modified Compton scattering x-ray attenuation profile, for performing a thickness compensation of the modified photoelectric absorption attenuation profile and modified Compton scattering x-ray attenuation profile using the surface profile, and for applying threshold levels to the thickness compensated modified photoelectric absorption attenuation profile and thickness compensated modified Compton scattering x-ray attenuation profile.

4. The apparatus of claim 3 wherein the surface profiling means is a laser profilometer.

5. The apparatus of claim 3 wherein the surface profiling means is a laser rangefinder.

6. A density determining apparatus for detecting a higher density object in a lower density meat product comprising:
   a) a first x-ray source producing x-rays of a first energy;
   b) a first linear x-ray detector for obtaining a first line scan x-ray attenuation profile along a plane through the meat product using the first energy x-rays;
   c) at least a second x-ray source producing x-rays of a second energy;
   d) at least a second linear x-ray detector for obtaining a second line scan x-ray attenuation profile in the same plane through the meat product using the second energy x-rays;
   e) a surface profiling means for obtaining a surface profile of the meat product in the same plane through the meat product;
   g) a processor for linearly combining the line scan x-ray attenuation profiles to obtain an enhanced line scan x-ray attenuation profile, for performing a thickness compensation of the enhanced line scan x-ray attenuation profile, and for applying a threshold level to the thickness compensated enhanced line scan x-ray attenuation profile.

7. The apparatus of claim 6 wherein the surface profiling means is a laser profilometer.

8. The apparatus of claim 6 wherein the surface profiling means is a laser rangefinder.

* * * * *